(12) United States Patent  
Bieringer et al.

(10) Patent No.: US 8,158,558 B2  
(45) Date of Patent: Apr. 17, 2012

(54) HERBICIDE COMBINATIONS COMPRISING SPECIFIC SULFONYLUREAS

(75) Inventors: Hermann Bieringer, Eppstein (DE); Hans Philipp Huff, Eppstein (DE); Erwin Hacker, Hochheim (DE)

(73) Assignee: Bayer CropScience GmbH, Frankfurt (DE)

( * ) Notice: Subject to any disclaimer, the term of this patent is extended or adjusted under 35 U.S.C. 154(b) by 786 days.

(21) Appl. No.: 10/198,580

(22) Filed: Jul. 18, 2002

(65) Prior Publication Data

US 2003/0060367 A1    Mar. 27, 2003

(30) Foreign Application Priority Data

Jul. 21, 2001 (DE) .................................. 101 35 642

(51) Int. Cl.
  *A01N 43/60* (2006.01)
  *A01N 43/64* (2006.01)
(52) U.S. Cl. .................. 504/133; 504/134; 504/136
(58) Field of Classification Search .............. 504/133, 504/134, 135, 136
   See application file for complete search history.

(56) References Cited

U.S. PATENT DOCUMENTS 6,211,118 B1  4/2001 Hoshi
6,221,809 B1 * 4/2001 Hacker et al. ............... 504/136

FOREIGN PATENT DOCUMENTS

| DE | 198 32 017 A1 | | 1/2000 |
|----|---|---|---|
| WO | 92/13845 | * | 8/1992 |
| WO | WO 92/13845 | | 8/1992 |
| WO | 95/10507 | * | 4/1995 |
| WO | WO 95/10507 | | 4/1995 |
| WO | WO 96/41537 | | 12/1996 |
| WO | WO 98/24320 | | 6/1998 |
| WO | WO 01/89301 A1 | | 11/2001 |
| WO | WO 02/01957 | | 1/2002 |
| WO | 02/17719 | * | 2/2002 |
| WO | WO 02/17719 A2 | | 3/2002 |

OTHER PUBLICATIONS

Amann, Z. PaKaKranke, PaSchuta, English translation(special issue XVII (2000), pp. 545-553.*
Pesticide Manual, British Crop Protection Council, 12th edition, 200 (pp. 181-182, 193-194, 420-421, 427-428, 434-435 and 742-743).*

* cited by examiner

*Primary Examiner* — Sabiha Qazi
(74) *Attorney, Agent, or Firm* — Frommer Lawrence & Haug LLP

(57) ABSTRACT

Herbicide combinations comprising an amount of components (A) and (B) have improved herbicidal action:
(A) one or more herbicides of the formula (I) or salts thereof

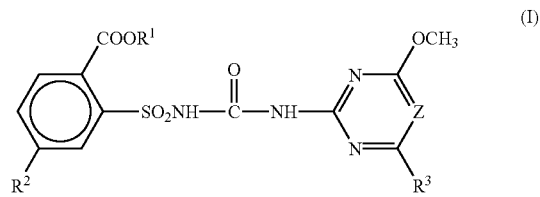

in which
$R^1$ is $(C_1-C_8)$-alkyl, $(C_3-C_4)$-alkenyl, $(C_3-C_4)$-alkynyl or $(C_1-C_4)$-alkyl which is mono- to tetrasubstituted by radicals selected from the group consisting of halogen and/or $(C_1-C_2)$-alkoxy,
$R^2$ is I or $CH_2NHSO_2CH_3$,
$R^3$ is methyl or methoxy and
Z is N or CH;
and
(B) denotes one or more herbicides which act selectively in some monocotyledonous crops against monocotyledonous and/or dicotyledonous harmful plants, which herbicides are selected from the group of compounds consisting of
(B1) flucarbazone,
(B2) BAY MKH 6561 (procarbazone),
(B3) florasulam,
(B4) halosulfuron,
(B5) tritosulfuron,
(B6) picolinafen,
(B7) cinidon-ethyl,
(B8) mesotrione,
(B9) metosulam,
(B10) clopyralid,
(B11) flufenacet,
(B12) flumetsulam,
(B13) flupoxam,
(B14) prosulfocarb,
(B15) flurtamone,
(B16) aclonifen,
(B17) hexazinone,
(B18) asulam,
(B19) diuron,
(B20) ametryn,
(B21) isoxaflutole,
(B22) amicarbazone and
(B23) trifloxysulfuron,
except for herbicide combinations comprising (A) one or more herbicides selected from the group consisting of the compounds of the formula (I) and their salts in which $R^1=(C_1-C_8)$-alkyl, $(C_3-C_4)$-alkenyl, $(C_3-C_4)$-alkynyl or $(C_1-C_4)$-alkyl which is mono- to tetrasubstituted by radicals selected from the group consisting of halogen and $(C_1-C_2)$-alkoxy, $R^2=CH_2NHSO_2CH_3$, $R^3=$methoxy and Z=CH, and (B) one or more herbicides selected from the group of the compounds metosulam (B9), flupoxam (B13), prosulfocarb (B14) and flurtamone (B15).

15 Claims, No Drawings

HERBICIDE COMBINATIONS COMPRISING SPECIFIC SULFONYLUREAS

The invention is in the technical field of crop protection products which can be employed against harmful plants, for example in crop plants, and which comprise, as active compounds, a combination of at least two herbicides.

The documents WO 92/13845 and WO 95/10507 disclose sulfonylureas and their salts and also their use as herbicides and/or plant growth regulators.

The efficacy of these herbicides against harmful plants in the crop plants is at a high level, but depends in general on the application rate, the formulation in question, the harmful plants or spectrum of harmful plants to be controlled in each case, the climatic conditions, the soil conditions and the like. Another criterion is the duration of action, or the breakdown rate of the herbicide. If appropriate, changes in the sensitivity of harmful plants, which may occur upon prolonged use of the herbicides or within geographic limitations must also be taken into consideration. The compensation of losses in action in the case of individual harmful plants by increasing the application rates of the herbicides is only possible to a certain degree, for example because such a procedure frequently reduces the selectivity of the herbicides or because the action is not improved, even when applying higher rates. In some cases, the selectivity in crops can be improved by adding safeners. In general, however, there remains a need for methods to achieve the herbicidal action with a lower application rate of active compounds. Not only does a lower application rate reduce the amount of an active compound required for application, but, as a rule, it also reduces the amount of formulation auxiliaries required. It both reduces the economic input and improves the ecological compatibility of the herbicide treatment.

One possibility of improving the application profile of a herbicide can consist in combining the active compound with one or more other active compounds. However, the combined use of a plurality of active compounds frequently causes phenomena of physical and biological incompatibility, for example a lack of stability in a coformulation, decomposition of an active compound, or antagonism of the active compounds. What is desired are, in contrast, combinations of active compounds having an advantageous activity profile, high stability and, if possible, a synergistically improved action, which allows the application rate to be reduced in comparison with the individual application of the active compounds to be combined.

Surprisingly, it has now been found that certain active compounds from the group of the sulfonylureas or their salts in combination with certain structurally different herbicides act together in a particularly advantageous manner, for example when they are employed in crop plants which are suitable for the selective use of the herbicides, if appropriate with addition of safeners.

The invention therefore provides herbicide combinations comprising an effective amount of components (A) and (B), where (A) denotes one or more herbicides selected from the group of the compounds of the formula (I) and their salts

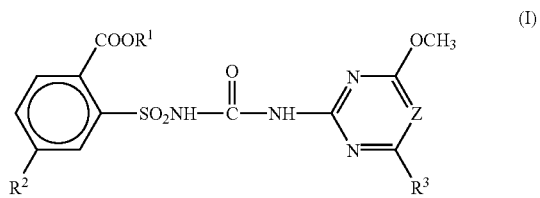

in which
$R^1$ is $(C_1-C_8)$-alkyl, $(C_3-C_4)$-alkenyl, $(C_3-C_4)$-alkynyl or $(C_1-C_4)$-alkyl which is mono- to tetrasubstituted by radicals selected from the group consisting of halogen and/or $(C_1-C_2)$-alkoxy, preferably $(C_1-C_4)$-alkyl,
$R^2$ is I or $CH_2NHSO_2CH_3$,
$R^3$ is methyl or methoxy and
Z is N or CH;
and
(B) denotes one or more herbicides which act selectively in some monocotyledonous crops against monocotyledonous and/or dicotyledonous harmful plants, which herbicides are selected from the group of compounds consisting of (refer to by the common name, and with a literature reference, for example from "The Pesticide Manual", 12th Ed., British Crop Protection Council 2000, abbreviated as "PM")

(B1) flucarbazone, in particular also comprising its salts, such as the sodium salt (PM, pp. 427-428), for example 4,5-dihydro-3-methoxy-4-methyl-5-oxo-N-(2-trifluoromethoxyphenylsulfonyl)-1H-1,2,4-triazole-1-carboxamide sodium salt (application rate generally: 1-500 g of AS/ha, preferably 5-200 g of AS/ha; ratio of application rates A:B generally=1:200-5:1, preferably 1:100-2:1);

(B2) BAY MKH 6561 (procarbazone), in particular also comprising its esters and salts, such as the sodium salt (Z. PflKrankh. PflSchutz, special edition XVII, 545-553 (2000)), for example methyl 2-({[(4-methyl-5-oxo-3-propoxy-4,5-dihydro-1H-1,2,4-triazol-1-yl)carbonyl]amino}sulfonyl)benzoate sodium salt (application rate generally: 1-500 g of AS/ha, preferably 5-200 g of AS/ha; ratio of application rates A:B generally=1:200-5:1, preferably 1:100-2:1);

(B3) florasulam, in particular also comprising its salts, such as the sodium salt (PM, pp. 420-421), for example 2',6',8'-trifluoro-5-methoxy[1,2,4]triazolo[1,5-c]pyrimidine-2-sulfanilide, (application rate generally: 1-500 g of AS/ha, preferably 1-50 g of AS/ha; ratio of application rates A:B generally=1:200-5:1, preferably 1:100-2:1);

(B4) halosulfuron, in particular also comprising its esters, such as halosulfuron-methyl, and its salts, such as the sodium salt (PM, pp. 497-499), for example methyl 3-chloro-5-(4,6-dimethoxypyrimidin-2-ylcarbamoylsulfamoyl)-1-methylpyrazole-4-carboxylate, (application rate generally: 1-500 g of AS/ha, preferably 5-200 g of AS/ha; ratio of application rates A:B generally=1:200-5:1, preferably 1:100-2:1);

(B5) tritosulfuron, in particular also comprising its esters and salts, such as the sodium salt (AG Chem, New Compound Review (publ. Agranova), Vol. 17, 1999, p. 24), for example N-[[[4'-methoxy-6-(trifluoromethyl)-1,3,5-triazin-2-yl]amino]carbonyl]-2-trifluoromethylbenzenesulfonamide, (application rate generally: 1-500 g of AS/ha, preferably 5-200 g of AS/ha; ratio of application rates A:B generally=1:200-5:1, preferably 1:100-2:1);

(B6) picolinafen, in particular also comprising its salts, such as the sodium salt (PM, pp. 742-743), for example 4'-fluoro-6-[($\alpha,\alpha,\alpha$-trifluoro-m-tolyl)oxy]picolinanilide; (application rate generally: 1-500 g of AS/ha, preferably 5-200 g of AS/ha; ratio of application rates A:B generally=1:200-5:1, preferably 1:100-2:1);

(B7) cinidon-ethyl, in particular also comprising its salts, such as the sodium salt (PM, pp. 181-182), for example ethyl (Z)-2-chloro-3-[2-chloro-5-(1,2-cyclohex-1-enedicarboximido)phenyl]acrylate, (application rate generally: 1-500 g of AS/ha, preferably 10-200 g of AS/ha; ratio of application rates A:B generally=1:200-5:1, preferably 1:100-2:1);

(B8) mesotrione, in particular also comprising its salts (PM, p. 602), for example 2-(4-(mesyl-2-nitrobenzoyl)cyclohexane-1,3-dione, (application rate generally: 5-1000 g of AS/ha, preferably 50-600 g of AS/ha; ratio of application rates A:B generally=1:500-3:1, preferably 1:250-2:1);

(B9) metosulam, in particular also comprising its salts, such as the sodium salt (PM, pp. 640-641), for example 2',6'-dichloro-5,7-dimethoxy-3'-methyl[1,2,4]triazolo[1,5-a]pyrimidine-2-sulfanilide, (application rate generally: 1-500 g of AS/ha, preferably 10-300 g of AS/ha; ratio of application rates A:B generally=1:200-5:1, preferably 1:100-2:1);

(B10) clopyralid, in particular also comprising its esters and salts, such as the sodium salt (PM, pp. 193-194), for example 3,6-dichloropyridine-2-carboxylic acid, (application rate generally: 10-1000 g of AS/ha, preferably 20-800 g of AS/ha; ratio of application rates A:B generally=1:500-5:1, preferably 1:250-2:1);

(B11) flufenacet, in particular also comprising its salts, such as the sodium salt (PM, pp. 434-435), for example 4'-fluoro-N-isopropyl-2-(5-trifluoromethyl-1,3,4-thiadiazol-2-yloxy)acetanilide, (application rate generally: 50-5000 g of AS/ha, preferably 150-2000 g of AS/ha; ratio of application rates A:B generally=1:1000-5:1, preferably 1:500-2:1);

(B12) flumetsulam, in particular also comprising its salts, such as the sodium salt (PM, pp. 438-439), for example 2',6'-difluoro-5-methyl[1,2,4]triazolo[1,5-a]pyrimidine-2-sulfanilide, (application rate generally: 5-1000 g of AS/ha, preferably 10-600 g of AS/ha; ratio of application rates A:B generally=1:500-5:1, preferably 1:250-2:1);

(B13) flupoxam, in particular also comprising its salts, such as the sodium salt (PM, p. 999), for example 1-[4-chloro-3-(2,2,3,3,3-pentafluoropropoxymethyl)phenyl]-5-phenyl-1H-1,2,4-triazole-3-carboxamide, (application rate generally: 5-5000 g of AS/ha, preferably 20-3000 g of AS/ha; ratio of application rates A:B generally=1:1000-5:1, preferably 1:500-2:1);

(B14) prosulfocarb, in particular also comprising its salts (PM, pp. 786-787), for example S-benzyl dipropylthiocarbamate, (application rate generally: 50-5000 g of AS/ha, preferably 200-3000 g of AS/ha; ratio of application rates A:B generally=1:1000-5:1, preferably 1:500-2:1);

(B15) flurtamone, in particular also comprising its salts, such as the sodium salt (PM, p. 459), for example (RS)-5-methylamino-2-phenyl-4-($\alpha,\alpha,\alpha$-trifluoro-m-tolyl)furan-3(2H)-one, (application rate generally: 50-5000 g of AS/ha, preferably 200-3000 g of AS/ha); ratio of application rates A:B generally=1:1000-5:1, preferably 1:500-2:1);

(B16) aclonifen, in particular also comprising its salts, such as the sodium salt (PM, p. 14-15), for example 2-chloro-6-nitro-3-phenoxyaniline, (application rate generally: 50-5000 g of AS/ha, preferably 200-3000 g of AS/ha; ratio of application rates A:B generally=1:1000-5:1, preferably 1:500-2:1);

(B17) hexazinone, in particular also comprising its salts (PM, pp. 514-515), for example 3-cyclohexyl-6-dimethylamino-1-methyl-1,3,5-triazine-2,4-(1H,3H)-dione, (application rate generally: 100-5000 g of AS/ha, preferably 300-4000 g of AS/ha; ratio of application rates A:B generally 1:10000-1:1, preferably 1:4000-1:6);

(B18) asulam, in particular also comprising its salts, such as the sodium salt (PM, pp. 40-42), for example methyl sulfanilylcarbamate, (application rate generally: 100-5000 g of AS/ha, preferably 300-4000 g of AS/ha; ratio of application rates A:B generally 1:10000-1:1, preferably 1:4000-1:6);

(B19) diuron, in particular also comprising its salts (PM, pp. 331-332), for example 3-(3,4-dichlorophenyl)-1,1-dimethylurea, (application rate generally: 100-5000 g of AS/ha, preferably 300-4000 g of AS/ha; ratio of application rates A:B generally 1:10000-1:1, preferably 1:4000-1:6);

(B20) ametryn, in particular also comprising its salts (PM, pp. 27-28), for example $N^2$-ethyl-$N^4$-isopropyl-6-methylthio-1,3,5-triazine-2,4-diamine, (application rate generally: 100-5000 g of AS/ha, preferably 300-4000 g of AS/ha; ratio of application rates A:B generally 1:10000-1:1, preferably 1:4000-1:6);

(B21) isoxaflutole, in particular also comprising its salts (PM, pp. 563-564), for example 5-cyclopropyl-1,2-oxazol-4-yl $\alpha,\alpha,\alpha$-trifluoro-2-mesyl-p-tolyl ketone, (application rate generally: 5-500 g of AS/ha, preferably 20-300 g of AS/ha; ratio of application rates A:B generally 1:1000-20:1, preferably 1:300-2:1);

(B22) amicarbazone, in particular also comprising its salts (PM, pp. 28-29), for example 4-amino-N-tert-butyl-4,5-dihydro-3-isopropyl-5-oxo-1H-1,2,4-triazole-1-carboxamide, (application rate generally: 100-5000 g of AS/ha, preferably 200-4000 g of AS/ha; ratio of application rates A:B generally 1:10000-1:1, preferably 1:4000-1:4); and (B23) trifloxysulfuron, in particular also comprising its salts, such as the sodium salt (The British Crop Protection Conference (12-15 Nov., 2001) Conference Proceedings Volume 1, pages 29-31), for example [N-[(4,6-dimethoxy-2-pyrimidinyl)carbamoyl]-3-(2,2,2-trifluoroethoxy)pyridine-2-sulfonamide sodium salt], (application rate generally: 1-5000 g of AS/ha, preferably 2-4000 g of AS/ha; ratio of application rates A:B generally 1:10000-100:1, preferably 1:4000-25:1), except for herbicide combinations comprising (A) one or more herbicides selected from the group consisting of the compounds of the formula (I) and their salts in which $R^1=(C_1-C_8)$-alkyl, $(C_3-C_4)$-alkenyl, $(C_3-C_4)$-alkynyl or $(C_1-C_4)$-alkyl which is mono- to tetrasubstituted by radicals selected from the group consisting of halogen and $(C_1-C_2)$-alkoxy, $R^2=CH_2NHSO_2CH_3$, $R^3=$methoxy and Z=CH, and (B) one or more herbicides selected from the group of the compounds metosulam (B9), flupoxam (B13), prosulfocarb (B14) and flurtamone (B15).

The herbicide combinations according to the invention comprise a herbicidally effective amount of components (A) and (B) and may comprise further components, for example agrochemically active compounds of a different type and/or formulation auxiliaires and/or additives customary in crop protection, or they may be employed together with these.

In a preferred embodiment, the herbicide combinations according to the invention have synergistic effects. The synergistic effects are observed, for example, when the active compounds (A) and (B) are applied together, but they can frequently also be observed when the compounds are applied as a split application over time. Another possibility is the application of the individual herbicides or the herbicide combinations in a plurality of portions (sequential application), for example after pre-emergence applications, followed by post-emergence applications or after early post-emergence applications, followed by applications at medium or late post-emergence. Preferred is the simultaneous or nearly simultaneous application of the active compounds of the herbicide combination according to the invention.

The synergistic effects allow the application rates of the individual active compounds to be reduced, a more potent action at the same application rate, the control of hitherto uncontrolable species (activity gaps), an extended application period and/or a reduced number of individual applications required and—as a result for the user—more advantageous weed control systems both from an economical and ecological point of view.

The abovementioned formula (I) includes all stereoisomers and their mixtures, in particular also racemic mixtures and—if enantiomers are possible—the respective biologically active enantiomer. The compounds of the formula (I) are capable of forming salts, for example salts in which the hydrogen of the —$SO_2$—NH— group is replaced by an agriculturally suitable cation. These salts are, for example, metal salts, in particular alkali metal salts or alkaline earth metal salts, especially sodium salts and potassium salts, or else ammonium salts or salts with organic amines. Salt formation may also occur by formation of an adduct of an acid and basic groups, such as, for example, amino and alkylamino. Acids which are suitable for this purpose are strong inorganic and organic acids, for example HCl, HBr, $H_2SO_4$ or $HNO_3$.

Compounds of the formula (I) and their salts and also their preparation are described, for example, in WO 92/13845 and WO 95/10507. Preferred compounds of the formula (I) and their salts are those in which $R^1$=($C_1$-$C_4$)-alkyl, preferably methyl, $R^2$=iodine, $R^3$=methyl and Z=N, and those in which $R^1$=($C_1$-$C_4$)-alkyl, preferably methyl, $R^2$=$CH_2NHSO_2CH_3$, $R^3$=methoxy and Z=CH. Examples of preferred compounds of the formula (I) and their salts are methyl 2-[3-(4,6-dimethoxypyrimidin-2-yl)ureidosulfonyl]4-methane-sulfone-aminomethyl-benzoate (mesosulfuron-methyl, A1.1) and its sodium salt (A1.2) (see, for example, WO 95/10507 and Agrow No. 347, Mar. 3, 2000, page 22 (PJB Publications Ltd. 2000) and 3-(4-methoxy-6-methyl-1,3,5-triazin-2-yl)-1-(2-methoxycarbonyl-5-iodophenylsulfonyl) urea (iodosulfuron-methyl, A2.1) and its sodium salt (A2.2) (see, for example, WO 92/13845 and PM, pp. 547-548).

The abovementioned active compounds of the formula (I) and their salts are capable of inhibiting the enzyme acetolactate synthase (ALS) and thus protein synthesis in plants. The application rate of the active compounds of the formula (I) and their salts can be varied within a wide range, for example between 0.001 and 0.5 kg of AS/ha (AS/ha means active substance per hectare=based on 100% active compound). In the case of applications at application rates of 0.01 to 0.2 kg of AS/ha of the active compounds of the formula (I) and their salts, preferably the active compounds (A1.1), (A1.2), (A2.1) and (A2.2), a relatively broad spectrum of annual and perennial broad-leaved weeds, weed grasses and Cyperacea is controlled pre- and post-emergence. In the combinations according to the invention, the application rates are generally lower, for example in the range from 0.5 to 120 g of AS/ha, preferably from 1 to 50 g of AS/ha.

The herbicides of component B) are, for example, sulfonamides, for example from the group of the sulfonylureas, such as halosulfuron, tritosulfuron and trifloxysulfuron, or from the group of the sulfanilides, such as florasulam, flumetsulam and metosulam, carboxamides, such as flupoxam and cinidon-ethyl, or urea derivatives, such as diuron, flucarbazone, procarbazone and amicarbazone, benzoyl derivatives, such as mesotrione and isoxaflutole, carbamates, such as prosulfocarb and asulam, aniline derivatives, such as picolinafen, flufenacet and aclonifen, triazine derivatives, such as hexazinone and ametryn, or other compounds, such as clopyralid and flurtamone.

The active compounds can generally be formulated as water-soluble wettable powders (WP), water-dispersible granules (WDG), water-emulsifiable granules (WEG), suspoemulsion (SE) or oil suspension concentrate (SC).

The ratios of the application rates A:B which are generally used are stated hereinabove and identify the weight ratio of the two components A and B to each other.

For use of the active compounds of the formula (I) or their salts in plant crops, it is expedient, depending on the plant crop, to apply a safener from certain application rates upward in order to reduce or to avoid possible damage to the crop plants. Examples of suitable safeners are those which have a safener action in combination with sulfonylurea herbicides, preferably phenylsulfonylureas. Suitable safeners are disclosed in WO-A-96/14747 and the literature cited therein.

The following groups of compounds are examples of suitable safeners for the abovementioned herbicidally active compounds (A):

a) Compounds of the dichlorophenylpyrazoline-3-carboxylic acid (S1) type, preferably compounds such as ethyl 1-(2,4-dichlorophenyl)-5-(ethoxycarbonyl)-5-methyl-2-pyrazoline-3-carboxylate (S1-1, mefenpyr-diethyl), and related compounds as they are described for example in WO 91/07874 and PM (pp. 594-595).

b) Dichlorophenylpyrazolecarboxylic acid derivatives, preferably compounds such as ethyl 1-(2,4-dichlorophenyl)-5-methylpyrazole-3-carboxylate (S1-2), ethyl 1-(2,4-dichlorophenyl)-5-isopropylpyrazole-3-carboxylate (S1-3), ethyl 1-(2,4-dichlorophenyl)-5-(1,1-dimethylethyl)pyrazole-3-carboxylate (S1-4), ethyl 1-(2,4-dichlorophenyl)-5-phenylpyrazole-3-carboxylate (S1-5) and related compounds as are described in EP-A-333 131 and EP-A-269 806.

c) Compounds of the triazolecarboxylic acid (S1) type, preferably compounds such as fenchlorazole, i.e. ethyl 1-(2,4-dichlorophenyl)-5-trichloromethyl-(1H)-1,2,4-triazole-3-carboxylate (S1-6) and related compounds (see EP-A-174 562 and EP-A-346 620).

d) Compounds of the 5-benzyl- or 5-phenyl-2-isoxazoline-3-carboxylic acid type or of the 5,5-diphenyl-2-isoxazoline-3-carboxylic acid type, preferably compounds such as ethyl 5-(2,4-dichlorobenzyl)-2-isoxazoline-3-carboxylate (S1-7) or ethyl 5-phenyl-2-isoxazoline-3-carboxylate (S1-8) and related compounds as are described in WO 91/08202, or of ethyl 5,5-diphenyl-2-isoxazoline-3-carboxylate (S1-9, isoxadifen-ethyl) or n-propyl 5,5-diphenyl-2-isoxazoline-3-carboxylate (S1-10) or ethyl 5-(4-fluorophenyl)-5-phenyl-2-isoxazoline-3-carboxylate (S1-11), as are described in patent application (WO-A-95/07897).

e) Compounds of the 8-quinoline oxyacetic acid (S2) type, preferably 1-methylhex-1-yl (5-chloro-8-quinolinoxy)acetate (S2-1, cloquintocetmexyl, e.g. PM (pp. 195-196), (1,3-dimethylbut-1-yl) (5-chloro-8-quinolinoxy)acetate (S2-2), 4-allyloxybutyl (5-chloro-8-quinolinoxy)acetate (S2-3), 1-allyloxyprop-2-yl (5-chloro-8-quinolinoxy)acetate (S2-4), ethyl (5-chloro-8-quinolinoxy)acetate (S2-5), methyl (5-chloro-8-quinolinoxy)acetate (S2-6), allyl (5-chloro-8-quinolinoxy)acetate (S2-7), 2-(2-propylideneiminooxy)-1-ethyl (5-chloro-8-quinolinoxy)acetate (S2-8), 2-oxoprop-1-yl (5-chloro-8-quinolinoxy) acetate (S2-9) and related compounds as are described in EP-A-86 750, EP-A-94 349 and EP-A-191 736 or EP-A-0 492 366.

f) Compounds of the (5-chloro-8-quinolinoxy)malonic acid type, preferably compounds such as diethyl (5-chloro-8-quinolinoxy)malonate, diallyl (5-chloro-8-quinolinoxy)malonate, methyl ethyl (5-chloro-8-quinolinoxy)-malonate and related compounds as are described in EP-A-0 582 198.

g) Active compounds of the phenoxyacetic acids, phenoxypropionic acids or aromatic carboxylic acids type, such as, for example, 2,4-dichlorophenoxyacetic acid (and esters) (2,4-D), 4-chloro-2-methylphenoxypropionic esters (mecoprop), MCPA or 3,6-dichloro-2-methoxybenzoic acid (and esters) (dicamba).

In many cases, the abovementioned safeners are also suitable for active compounds of group (B). In addition, the following safeners are suitable for the herbicide combinations according to the invention:

h) active compounds of the pyrimidine type, such as, for example,
"fenclorim" (PM, pp. 386-387) (=4,6-dichloro-2-phenylpyrimidine), i) active compounds of the dichloroacetamide type, which are frequently used as pre-emergence safeners (soil-acting safeners) such as, for example,
"dichloromid" (PM, pp. 270-271) (=N,N-diallyl-2,2-dichloroacetamide),
"AR-29148" (=3-dichloroacetyl-2,2,5-trimethyl-1,3-oxazolidone by Stauffer),
"benoxacor" (PM, pp. 74-75) (=4-dichloroacetyl-3,4-dihydro-3-methyl-2H-1,4-benzoxazine),
"APPG-1292" (=N-allyl-N[(1,3-dioxolan-2-yl)-methyl]dichloroacetamide by PPG Industries),
"ADK-24" (=N-allyl-N-[(allylaminocarbonyl)-methyl]-dichloroacetamide by Sagro-Chem),
"AAD-67" or "AMON 4660" (=3-dichloroacetyl-1-oxa-3-azaspiro[4,5]decane by Nitrokemia or Monsanto),
"diclonon" or "ABAS145138" or "ALAB145138" (=(=3-dichloroacetyl-2,5,5-trimethyl-1,3-diazabicyclo[4.3.0]nonane by BASF) and
"furilazol" or "AMON 13900" (see PM, 482-483) (=(RS)-3-dichloroacetyl-5-(2-furyl)-2,2-dimethyloxazolidone)

j) active compounds of the dichloroacetone derivatives type, such as, for example,
"AMG 191" (CAS Reg. No. 96420-72-3) (=2-dichloromethyl-2-methyl-1,3-dioxolane by Nitrokemia), k) active compounds of the oxyimino compounds type which are known as seed-dressing materials such as, for example,
"oxabetrinil" (PM, p. 689) (=(Z)-1,3-dioxolan-2-yl-methoxyimino(phenyl)acetonitrile), which is known as safener in seed dressing to prevent metolachlor damage,
"fluxofenim" (PM, pp. 467-468) (=1-(4-chlorophenyl)-2,2,2-trifluoro-1-ethanone O-(1,3-dioxolan-2-ylmethyl)-oxime, which is known as safener in seed dressing to prevent metolachlor damage, and
"cyometrinil" or "A-CGA-43089" (PM, p. 983) (=(Z)-cyanomethoxyimino(phenyl)acetonitrile), which is known as safener in seed dressing to prevent metolachlor damage, l) active compounds of the thiazolecarboxylic esters type, which are known as seed-dressing materials, such as, for example,
"flurazol" (PM, pp. 450-451) (=benzyl 2-chloro-4-trifluoromethyl-1,3-thiazole-5-carboxylate), which is known as safener in seed dressing to prevent alachlor and metolachlor damage, m) active compounds of the naphthalenedicarboxylic acid derivatives type which are known as seed-dressing agents, such as, for example,
"naphthalic anhydride" (PM, pp. 1009-1010) (=1,8-naphthalenedicarboxylic anhydride), which is known as safener for maize in seed dressing to prevent thiocarbamate herbicide damage, n) active compounds of the chromaneacetic acid derivatives type, such as, for example,
"ACL 304415" (CAS Reg. No. 31541-57-8) (=2-84-carboxychroman-4-yl)acetic acid by American Cyanamid), o) active compounds which, in addition to a herbicidal action against harmful plants, also have a safener action on crop plants, such as, for example,
"dimepiperate" or "AMY-93" (PM, pp. 302-303) (=S-1-methyl-1-phenylethyl piperidine-1-carbothioate),
"daimuron" or "ASK 23" (PM, p. 247) (=1-(1-methyl-1-phenylethyl)-3-p-tolylurea),
"cumyluron"="AJC-940" (=3-(2-chlorophenylmethyl)-1-(1-methyl-1-phenyl-ethyl)urea, see JP-A-60087254),
"methoxyphenon" or "ANK 049" (=3,3'-dimethyl-4-methoxybenzophenone),
"CSB" (=1-bromo-4-(chloromethylsulfonyl)benzene) (CAS Reg. No. 54091-06-4 by Kumiai).

The active compounds (A), if appropriate in the presence of safeners, are suitable for controlling harmful plants in plant crops, for example in economically important crops such as cereals (such as wheat, barley, rye, oats, rice, corn, millet), sugar beet, sugar cane, oilseed rape, cotton and soya beans. Of particular interest is the application in monocotyledonous crops such as cereals, for example wheat, barley, rye, oats, rice, corn and millet. These crops are also preferred for the combinations (A)+(B).

When the short form of the common name of an active compound is used in the context of this description, all customary derivatives are included in this, such as the esters and salts, and isomers, in particular optical isomers, especially the commercially available form or forms. If the common name refers to an ester or salt, this includes in each case all other customary derivatives, such as other esters and salts, the free acids and neutral compounds, and isomers, in particular optical isomers, especially the commercially available form or forms. The chemical compound names stated designate at least one of the compounds included in the common name, frequently a preferred compound. In the case of sulfonamides such as sulfonylureas, salts also encompass those which are formed by replacement of a hydrogen atom on the sulfonamide group by a cation.

Also included according to the invention are those herbicide combinations which, in addition to components (A) and (B), also comprise one or more further agrochemically active compounds of a different structure, such as herbicides, insecticides, fungicides or safeners. To such combinations, the preferred conditions illustrated below in particular for combinations (A)+(B) according to the invention also primarily apply, if they comprise the combinations (A)+(B) according to the invention, and with respect to the combination (A)+(B) in question.

Of particular interest are herbicidal compositions comprising the following compounds (A)+(B):

(A1.1)+(B1), (A1.1)+(B2), (A1.1)+(B3), (A1.1)+(B4), (A1.1)+(B5), (A1.1)+(B6), (A1.1)+(B7), (A1.1)+(B8), (A1.1)+(B9), (A1.1)+(B10), (A1.1)+(B11), (A1.1)+(B12), (A1.1)+(B13), (A1.1)+(B14), (A1.1)+(B15), (A1.1)+(B16), (A1.1)+(B17), (A1.1)+(B18), (A1.1)+(B19), (A1.1)+(B20), (A1.1)+(B21), (A1.1)+(B22), (A1.1)+(B23);

(A1.2)+(B1), (A1.2)+(B2), (A1.2)+(B3), (A1.2)+(B4), (A1.2)+(B5), (A1.2)+(B6), (A1.2)+(B7), (A1.2)+(B8), (A1.2)+(B9), (A1.2)+(B10), (A1.2)+(B11), (A1.2)+(B12), (A1.2)+(B13), (A1.2)+(B14), (A1.2)+(B15), (A1.2)+(B16), (A1.2)+(B17), (A1.2)+(B18), (A1.2)+(B19), (A1.2)+(B20), (A1.2)+(B21), (A1.2)+(B22), (A1.2)+(B23);

(A2.1)+(B1), (A2.1)+(B2), (A2.1)+(B3), (A2.1)+(B4), (A2.1)+(B5), (A2.1)+(B6), (A2.1)+(B7), (A2.1)+(B8), (A2.1)+(B9), (A2.1)+(B10), (A2.1)+(B11), (A2.1)+(B12), (A2.1)+(B13), (A2.1)+(B14), (A2.1)+(B15), (A2.1)+(B16), (A2.1)+(B17), (A2.1)+(B18), (A2.1)+(B19), (A2.1)+(B20), (A2.1)+(B21), (A2.1)+(B22), (A2.1)+(B23);

(A2.2)+(B1), (A2.2)+(B2), (A2.2)+(B3), (A2.2)+(B4), (A2.2)+(B5), (A2.2)+(B6), (A2.2)+(B7), (A2.2)+(B8), (A2.2)+(B9), (A2.2)+(B10), (A2.2)+(B11), (A2.2)+(B12), (A2.2)+(B13), (A2.2)+(B14), (A2.2)+(B15), (A2.2)+(B16), (A2.2)+(B17), (A2.2)+(B18), (A2.2)+(B19), (A2.2)+(B20), (A2.2)+(B21), (A2.2)+(B22), (A2.2)+(B23);

(A1.1)+(A2.1)+(B1), (A1.1)+(A2.1)+(B2), (A1.1)+(A2.1)+(B3), (A1.1)+(A2.1)+(B4), (A1.1)+(A2.1)+(B5), (A1.1)+(A2.1)+(B6), (A1.1)+(A2.1)+(B7), (A1.1)+(A2.1)+(B8), (A1.1)+(A2.1)+(B9), (A1.1)+(A2.1)+(B10), (A1.1)+(A2.1)+(B11), (A1.1)+(A2.1)+(B12), (A1.1)+(A2.1)+(B13), (A1.1)+(A2.1)+(B14), (A1.1)+(A2.1)+(B15), (A1.1)+(A2.1)+(B16), (A1.1)+(A2.1)+(B17), (A1.1)+(A2.1)+(B18), (A1.1)+(A2.1)+(B19), (A1.1)+(A2.1)+(B20), (A1.1)+(A2.1)+(B21), (A1.1)+(A2.1)+(B22), (A1.1)+(A2.1)+(B23);

(A1.1)+(A2.2)+(B1), (A1.1)+(A2.2)+(B2), (A1.1)+(A2.2)+(B3), (A1.1)+(A2.2)+(B4), (A1.1)+(A2.2)+(B5), (A1.1)+(A2.2)+(B6), (A1.1)+(A2.2)+(B7), (A1.1)+(A2.2)+(B8), (A1.1)+(A2.2)+(B9), (A1.1)+(A2.2)+(B10), (A1.1)+(A2.2)+(B11), (A1.1)+(A2.2)+(B12), (A1.1)+(A2.2)+(B13), (A1.1)+(A2.2)+(B14), (A1.1)+(A2.2)+(B15), (A1.1)+(A2.2)+(B16), (A1.1)+(A2.2)+(B17), (A1.1)+(A2.2)+(B18), (A1.1)+(A2.2)+(B19), (A1.1)+(A2.2)+(B20), (A1.1)+(A2.2)+(B21), (A1.1)+(A2.2)+(B22), (A1.1)+(A2.2)+(B23);

(A2.1)+(A1.2)+(B1), (A2.1)+(A1.2)+(B2), (A2.1)+(A1.2)+(B3), (A2.1)+(A1.2)+(B4), (A2.1)+(A1.2)+(B5), (A2.1)+(A1.2)+(B6), (A2.1)+(A1.2)+(B7), (A2.1)+(A1.2)+(B8), (A2.1)+(A1.2)+(B9), (A2.1)+(A1.2)+(B10), (A2.1)+(A1.2)+(B11), (A2.1)+(A1.2)+(B12), (A2.1)+(A1.2)+(B13), (A2.1)+(A1.2)+(B14), (A2.1)+(A1.2)+(B15), (A2.1)+(A1.2)+(B16), (A2.1)+(A1.2)+(B17), (A2.1)+(A1.2)+(B18), (A2.1)+(A1.2)+(B19), (A2.1)+(A1.2)+(B20), (A2.1)+(A1.2)+(B21), (A2.1)+(A1.2)+(B22), (A2.1)+(A1.2)+(B23);

(A2.1)+(A2.2)+(B1), (A2.1)+(A2.2)+(B2), (A2.1)+(A2.2)+(B3), (A2.1)+(A2.2)+(B4), (A2.1)+(A2.2)+(B5), (A2.1)+(A2.2)+(B6), (A2.1)+(A2.2)+(B7), (A2.1)+(A2.2)+(B8), (A2.1)+(A2.2)+(B9), (A2.1)+(A2.2)+(B10), (A2.1)+(A2.2)+(B11), (A2.1)+(A2.2)+(B12), (A2.1)+(A2.2)+(B13), (A2.1)+(A2.2)+(B14), (A2.1)+(A2.2)+(B15), (A2.1)+(A2.2)+(B16), (A2.1)+(A2.2)+(B17), (A2.1)+(A2.2)+(B18), (A2.1)+(A2.2)+(B19), (A2.1)+(A2.2)+(B20), (A2.1)+(A2.2)+(B21), (A2.1)+(A2.2)+(B22), (A2.1)+(A2.2)+(B23).

Here, the ranges of application rates and ratios of application rates mentioned above are in each case preferred. In addition, each of the abovementioned 2-component and 3-component combinations may comprise one or more safeners, in particular a safener such as mefenpyr-diethyl (S1-1), isoxadifen-ethyl (S1-9) and cloquintocetmexyl (S2-1):

(A1.1)+(B1)+(S1-1), (A1.1)+(B2)+(S1-1), (A1.1)+(B3)+(S1-1), (A1.1)+(B4)+(S1-1), (A1.1)+(B5)+(S1-1), (A1.1)+(B6)+(S1-1), (A1.1)+(B7)+(S1-1), (A1.1)+(B8)+(S1-1), (A1.1)+(B9)+(S1-1), (A1.1)+(B10)+(S1-1), (A1.1)+(B11)+(S1-1), (A1.1)+(B12)+(S1-1), (A1.1)+(B13)+(S1-1), (A1.1)+(B14)+(S1-1), (A1.1)+(B15)+(S1-1), (A1.1)+(B16)+(S1-1), (A1.1)+(B17)+(S1-1), (A1.1)+(B18)+(S1-1), (A1.1)+(B19)+(S1-1), (A1.1)+(B20)+(S1-1), (A1.1)+(B21)+(S1-1), (A1.1)+(B22)+(S1-1), (A1.1)+(B23)+(S1-1);

(A1.2)+(B1)+(S1-1), (A1.2)+(B2)+(S1-1), (A1.2)+(B3)+(S1-1), (A1.2)+(B4)+(S1-1), (A1.2)+(B5)+(S1-1), (A1.2)+(B6)+(S1-1), (A1.2)+(B7)+(S1-1), (A1.2)+(B8)+(S1-1), (A1.2)+(B9)+(S1-1), (A1.2)+(B10)+(S1-1), (A1.2)+(B11)+(S1-1), (A1.2)+(B12)+(S1-1), (A1.2)+(B13)+(S1-1), (A1.2)+(B14)+(S1-1), (A1.2)+(B15)+(S1-1), (A1.2)+(B16)+(S1-1), (A1.2)+(B17)+(S1-1), (A1.2)+(B18)+(S1-1), (A1.2)+(B19)+(S1-1), (A1.2)+(B20)+(S1-1), (A1.2)+(B21)+(S1-1), (A1.2)+(B22)+(S1-1), (A1.2)+(B23)+(S1-1);

(A2.1)+(B1)+(S1-1), (A2.1)+(B2)+(S1-1), (A2.1)+(B3)+(S1-1), (A2.1)+(B4)+(S1-1), (A2.1)+(B5)+(S1-1), (A2.1)+(B6)+(S1-1), (A2.1)+(B7)+(S1-1), (A2.1)+(B8)+(S1-1), (A2.1)+(B9)+(S1-1), (A2.1)+(B10)+(S1-1), (A2.1)+(B11)+(S1-1), (A2.1)+(B12)+(S1-1), (A2.1)+(B13)+(S1-1), (A2.1)+(B14)+(S1-1), (A2.1)+(B15)+(S1-1), (A2.1)+(B16)+(S1-1), (A2.1)+(B17)+(S1-1), (A2.1)+(B18)+(S1-1), (A2.1)+(B19)+(S1-1), (A2.1)+(B20)+(S1-1), (A2.1)+(B21)+(S1-1), (A2.1)+(B22)+(S1-1), (A2.1)+(B23)+(S1-1);

(A2.2)+(B1)+(S1-1), (A2.2)+(B2)+(S1-1), (A2.2)+(B3)+(S1-1), (A2.2)+(B4)+(S1-1), (A2.2)+(B5)+(S1-4), (A2.2)+(B6)+(S1-1), (A2.2)+(B7)+(S1-1), (A2.2)+(B8)+(S1-1), (A2.2)+(B9)+(S1-1), (A2.2)+(B10)+(S1-1), (A2.2)+(B11)+(S1-1), (A2.2)+(B12)+(S1-1), (A2.2)+(B13)+(S1-1), (A2.2)+(B14)+(S1-1), (A2.2)+(B15)+(S1-1), (A2.2)+(B16)+(S1-1), (A2.2)+(B17)+(S1-1), (A2.2)+(B18)+(S1-1), (A2.2)+(B19)+(S1-1), (A2.2)+(B20)+(S1-1), (A2.2)+(B21)+(S1-1), (A2.2)+(B22)+(S1-1), (A2.2)+(B23)+(S1-1);

(A1.1)+(A2.1)+(B1)+(S1-1), (A1.1)+(A2.1)+(B2)+(S1-1), (A1.1)+(A2.1)+(B3)+(S1-1), (A1.1)+(A2.1)+(B4)+(S1-1), (A1.1)+(A2.1)+(B5)+(S1-1), (A1.1)+(A2.1)+(B6)+(S1-1), (A1.1)+(A2.1)+(B7)+(S1-1), (A1.1)+(A2.1)+(B8)+(S1-1), (A1.1)+(A2.1)+(B9)+(S1-1), (A1.1)+(A2.1)+(B10)+(S1-1), (A1.1)+(A2.1)+(B11)+(S1-1), (A1.1)+(A2.1)+(B12)+(S1-1), (A1.1)+(A2.1)+(B13)+(S1-1), (A1.1)+(A2.1)+(B14)+(S1-1), (A1.1)+(A2.1)+(B15)+(S1-1), (A1.1)+(A2.1)+(B16)+(S1-1), (A1.1)+(A2.1)+(B17)+(S1-1), (A1.1)+(A2.1)+(B18)+(S1-1), (A1.1)+(A2.1)+(B19)+(S1-1), (A1.1)+(A2.1)+(B20)+(S1-1), (A1.1)+(A2.1)+(B21)+(S1-1), (A1.1)+(A2.1)+(B22)+(S1-1), (A1.1)+(A2.1)+(B23)+(S1-1);

(A1.1)+(A2.2)+(B1)+(S1-1), (A1.1)+(A2.2)+(B2)+(S1-1), (A1.1)+(A2.2)+(B3)+(S1-1), (A1.1)+(A2.2)+(B4)+(S1-1), (A1.1)+(A2.2)+(B5)+(S1-1), (A1.1)+(A2.2)+(B6)+(S1-1), (A1.1)+(A2.2)+(B7)+(S1-1), (A1.1)+(A2.2)+(B8)+(S1-1), (A1.1)+(A2.2)+(B9)+(S1-1), (A1.1)+(A2.2)+(B10)+(S1-1), (A1.1)+(A2.2)+(B11)+(S1-1), (A1.1)+(A2.2)+(B12)+(S1-1), (A1.1)+(A2.2)+(B13)+(S1-1), (A1.1)+(A2.2)+(B14)+(S1-1), (A1.1)+(A2.2)+(B15)+(S-1), (A1.1)+(A2.2)+(B16)+(S1-1), (A1.1)+(A2.2)+(B17)+(S1-1), (A1.1)+(A2.2)+(B18)+(S1-1), (A1.1)+(A2.2)+(B19)+(S1-1), (A1.1)+(A2.2)+(B20)+(S1-1), (A1.1)+(A2.2)+(B21)+(S1-1), (A1.1)+(A2.2)+(B22)+(S1-1), (A1.1)+(A2.2)+(B23)+(S1-1);

(A2.1)+(A1.2)+(B1)+(S1-1), (A2.1)+(A1.2)+(B2)+(S1-1), (A2.1)+(A1.2)+(B3)+(S1-1), (A2.1)+(A1.2)+(B4)+(S1-1), (A2.1)+(A1.2)+(B5)+(S1-1), (A2.1)+(A1.2)+(B6)+(S1-1), (A2.1)+(A1.2)+(B7)+(S1-1), (A2.1)+(A1.2)+(B8)+(S1-1), (A2.1)+(A1.2)+(B9)+(S1-1), (A2.1)+(A1.2)+(B10)+(S1-1), (A2.1)+(A1.2)+(B11)+(S1-1), (A2.1)+(A1.2)+(B12)+(S1-1), (A2.1)+(A1.2)+(B13)+(S1-1), (A2.1)+(A1.2)+(B14)+(S1-1), (A2.1)+(A1.2)+(B15)+(S1-1), (A2.1)+(A1.2)+(B16)+(S1-1), (A2.1)+(A1.2)+(B17)+(S1-1), (A2.1)+(A1.2)+(B18)+(S1-1), (A2.1)+(A1.2)+(B19)+(S1-1), (A2.1)+(A1.2)+(B20)+(S1-1), (A2.1)+(A1.2)+(B21)+(S1-1), (A2.1)+(A1.2)+(B22)+(S1-1), (A2.1)+(A1.2)+(B23)+(S1-1);

(A2.1)+(A2.2)+(B1)+(S1-1), (A2.1)+(A2.2)+(B2)+(S1-1), (A2.1)+(A2.2)+(B3)+(S1-1), (A2.1)+(A2.2)+(B4)+(S1-1), (A2.1)+(A2.2)+(B5)+(S1-1), (A2.1)+(A2.2)+(B6)+(S1-1), (A2.1)+(A2.2)+(B7)+(S1-1), (A2.1)+(A2.2)+(B8)+(S1-1), (A2.1)+(A2.2)+(B9)+(S1-1), (A2.1)+(A2.2)+(B10)+(S1-1), (A2.1)+(A2.2)+(B11)+(S1-1), (A2.1)+(A2.2)+(B12)+(S1-1), (A2.1)+(A2.2)+(B13)+(S1-1), (A2.1)+(A2.2)+(B14)+(S1-1), (A2.1)+(A2.2)+(B15)+(S1-1), (A2.1)+(A2.2)+(B16)+(S1-1), (A2.1)+(A2.2)+(B17)+(S1-1), (A2.1)+(A2.2)+(B18)+(S1-1), (A2.1)+(A2.2)+(B19)+(S1-1), (A2.1)+(A2.2)+(B20)+(S1-1), (A2.1)+(A2.2)+(B21)+(S1-1), (A2.1)+(A2.2)+(B22)+(S1-1), (A2.1)+(A2.2)+(B23)+(S1-1);

(A1.1)+(B1)+(S1-9), (A1.1)+(B2)+(S1-9), (A1.1)+(B3)+(S1-9), (A1.1)+(B4)+(S1-9), (A1.1)+(B5)+(S1-9), (A1.1)+(B6)+(S1-9), (A1.1)+(B7)+(S1-9), (A1.1)+(B8)+(S1-9), (A1.1)+(B9)+(S1-9), (A1.1)+(B10)+(S1-9), (A1.1)+(B11)+(S1-9), (A1.1)+(B12)+(S1-9), (A1.1)+(B13)+(S1-9), (A1.1)+(B14)+(S1-9), (A1.1)+(B15)+(S1-9), (A1.1)+(B16)+(S1-9), (A1.1)+(B17)+(S1-9), (A1.1)+(B18)+(S1-9), (A1.1)+(B19)+(S1-9), (A1.1)+(B20)+(S1-9), (A1.1)+(B21)+(S1-9), (A1.1)+(B22)+(S1-9), (A1.1)+(B23)+(S1-9);

(A1.2)+(B1)+(S1-9), (A1.2)+(B2)+(S1-9), (A1.2)+(B3)+(S1-9), (A1.2)+(B4)+(S1-9), (A1.2)+(B5)+(S1-9), (A1.2)+(B6)+(S1-9), (A1.2)+(B7)+(S1-9), (A1.2)+(B8)+(S1-9), (A1.2)+(B9)+(S1-9), (A1.2)+(B10)+(S1-9), (A1.2)+(B11)+(S1-9), (A1.2)+(B12)+(S1-9), (A1.2)+(B13)+(S1-9), (A1.2)+(B14)+(S1-9), (A1.2)+(B15)+(S1-9), (A1.2)+(B16)+(S1-9), (A1.2)+(B17)+(S1-9), (A1.2)+(B18)+(S1-9), (A1.2)+(B19)+(S1-9), (A1.2)+(B20)+(S1-9), (A1.2)+(B21)+(S1-9), (A1.2)+(B22)+(S1-9), (A1.2)+(B23)+(S1-9);

(A2.1)+(B1)+(S1-9), (A2.1)+(B2)+(S1-9), (A2.1)+(B3)+(S1-9), (A2.1)+(B4)+(S1-9), (A2.1)+(B5)+(S1-9), (A2.1)+(B6)+(S1-9), (A2.1)+(B7)+(S1-9), (A2.1)+(B8)+(S1-9), (A2.1)+(B9)+(S1-9), (A2.1)+(B10)+(S1-9), (A2.1)+(B11)+(S1-9), (A2.1)+(B12)+(S1-9), (A2.1)+(B13)+(S1-9), (A2.1)+(B14)+(S1-9), (A2.1)+(B15)+(S1-9), (A2.1)+(B16)+(S1-9), (A2.1)+(B17)+(S1-9), (A2.1)+(B18)+(S1-9), (A2.1)+(B19)+(S1-9), (A2.1)+(B20)+(S1-9), (A2.1)+(B21)+(S1-9), (A2.1)+(B22)+(S1-9), (A2.1)+(B23)+(S1-9);

(A2.2)+(B1)+(S1-9), (A2.2)+(B2)+(S1-9), (A2.2)+(B3)+(S1-9), (A2.2)+(B4)+(S1-9), (A2.2)+(B5)+(S1-9), (A2.2)+(B6)+(S1-9), (A2.2)+(B7)+(S1-9), (A2.2)+(B8)+(S1-9), (A2.2)+(B9)+(S1-9), (A2.2)+(B10)+(S1-9), (A2.2)+(B11)+(S1-9), (A2.2)+(B12)+(S1-9), (A2.2)+(B13)+(S1-9), (A2.2)+(B14)+(S1-9), (A2.2)+(B15)+(S1-9), (A2.2)+(B16)+(S1-9), (A2.2)+(B17)+(S1-9), (A2.2)+(B18)+(S1-9), (A2.2)+(B19)+(S1-9), (A2.2)+(B20)+(S1-9), (A2.2)+(B21)+(S1-9), (A2.2)+(B22)+(S1-9), (A2.2)+(B23)+(S1-9);

(A1.1)+(A2.1)+(B1)+(S1-9), (A1.1)+(A2.1)+(B2)+(S1-9), (A1.1)+(A2.1)+(B3)+(S1-9), (A1.1)+(A2.1)+(B4)+(S1-9), (A1.1)+(A2.1)+(B5)+(S1-9), (A1.1)+(A2.1)+(B6)+(S1-9), (A1.1)+(A2.1)+(B7)+(S1-9), (A1.1)+(A2.1)+(B8)+(S1-9), (A1.1)+(A2.1)+(B9)+(S1-9), (A1.1)+(A2.1)+(B10)+(S1-9), (A1.1)+(A2.1)+(B11)+(S1-9), (A1.1)+(A2.1)+(B12)+(S1-9), (A1.1)+(A2.1)+(B13)+(S1-9), (A1.1)+(A2.1)+(B14)+(S1-9), (A1.1)+(A2.1)+(B15)+(S1-9), (A1.1)+(A2.1)+(B16)+(S1-9), (A1.1)+(A2.1)+(B17)+(S1-9), (A1.1)+(A2.1)+(B18)+(S1-9), (A1.1)+(A2.1)+(B19)+(S1-9), (A1.1)+(A2.1)+(B20)+(S1-9), (A1.1)+(A2.1)+(B21)+(S1-9), (A1.1)+(A2.1)+(B22)+(S1-9), (A1.1)+(A2.1)+(B23)+(S1-9);

(A1.1)+(A2.2)+(B1)+(S1-9), (A1.1)+(A2.2)+(B2)+(S1-9), (A1.1)+(A2.2)+(B3)+(S1-9), (A1.1)+(A2.2)+(B4)+(S1-9), (A1.1)+(A2.2)+(B5)+(S1-9), (A1.1)+(A2.2)+(B6)+(S1-9), (A1.1)+(A2.2)+(B7)+(S1-9), (A1.1)+(A2.2)+(B8)+(S1-9), (A1.1)+(A2.2)+(B9)+(S1-9), (A1.1)+(A2.2)+(B10)+(S1-9), (A1.1)+(A2.2)+(B11)+(S1-9), (A1.1)+(A2.2)+(B12)+(S1-9), (A1.1)+(A2.2)+(B13)+(S1-9), (A1.1)+(A2.2)+(B14)+(S1-9), (A1.1)+(A2.2)+(B15)+(S1-9), (A1.1)+(A2.2)+(B16)+(S1-9), (A1.1)+(A2.2)+(B17)+(S1-9), (A1.1)+(A2.2)+(B18)+(S1-9), (A1.1)+(A2.2)+(B19)+(S1-9), (A1.1)+(A2.2)+(B20)+(S1-9), (A1.1)+(A2.2)+(B21)+(S1-9), (A1.1)+(A2.2)+(B22)+(S1-9), (A1.1)+(A2.2)+(B23)+(S1-9);

(A2.1)+(A1.2)+(B1)+(S1-9), (A2.1)+(A1.2)+(B2)+(S1-9), (A2.1)+(A1.2)+(B3)+(S1-9), (A2.1)+(A1.2)+(B4)+(S1-9), (A2.1)+(A1.2)+(B5)+(S1-9), (A2.1)+(A1.2)+(B6)+(S1-9), (A2.1)+(A1.2)+(B7)+(S1-9), (A2.1)+(A1.2)+(B8)+(S1-9), (A2.1)+(A1.2)+(B9)+(S1-9), (A2.1)+(A1.2)+(B10)+(S1-9), (A2.1)+(A1.2)+(B11)+(S1-9), (A2.1)+(A1.2)+(B12)+(S1-9), (A2.1)+(A1.2)+(B13)+(S1-9), (A2.1)+(A1.2)+(B14)+(S1-9), (A2.1)+(A1.2)+(B15)+(S1-9), (A2.1)+(A1.2)+(B16)+(S1-9), (A2.1)+(A1.2)+(B17)+(S1-9), (A2.1)+(A1.2)+(B18)+(S1-9), (A2.1)+(A1.2)+(B19)+(S1-9), (A2.1)+(A1.2)+(B20)+(S1-9), (A2.1)+(A1.2)+(B21)+(S1-9), (A2.1)+(A1.2)+(B22)+(S1-9), (A2.1)+(A1.2)+(B23)+(S1-9);

(A2.1)+(A2.2)+(B1)+(S1-9), (A2.1)+(A2.2)+(B2)+(S1-9), (A2.1)+(A2.2)+(B3)+(S1-9), (A2.1)+(A2.2)+(B4)+(S1-9), (A2.1)+(A2.2)+(B5)+(S1-9), (A2.1)+(A2.2)+(B6)+(S1-9), (A2.1)+(A2.2)+(B7)+(S1-9), (A2.1)+(A2.2)+(B8)+(S1-9), (A2.1)+(A2.2)+(B9)+(S1-9), (A2.1)+(A2.2)+(B10)+(S1-9), (A2.1)+(A2.2)+(B11)+(S1-9), (A2.1)+(A2.2)+(B12)+(S1-9), (A2.1)+(A2.2)+(B13)+(S1-9), (A2.1)+(A2.2)+(B14)+(S1-9), (A2.1)+

(A2.2)+(B15)+(S1-9), (A2.1)+(A2.2)+(B16)+(S1-9), (A2.1)+(A2.2)+(B17)+(S1-9), (A2.1)+(A2.2)+(B18)+(S1-9), (A2.1)+(A2.2)+(B19)+(S1-9), (A2.1)+(A2.2)+(B20)+(S1-9), (A2.1)+(A2.2)+(B21)+(S1-9), (A2.1)+(A2.2)+(B22)+(S1-9), (A2.1)+(A2.2)+(B23)+(S1-9);

(A1.1)+(B1)+(S2-1), (A1.1)+(B2)+(S2-1), (A1.1)+(B3)+(S2-1), (A1.1)+(B4)+(S2-1), (A1.1)+(B5)+(S2-1), (A1.1)+(B6)+(S2-1), (A1.1)+(B7)+(S2-1), (A1.1)+(B8)+(S2-1), (A1.1)+(B9)+(S2-1), (A1.1)+(B10)+(S2-1), (A1.1)+(B11)+(S2-1), (A1.1)+(B12)+(S2-1), (A1.1)+(B13)+(S2-1), (A1.1)+(B14)+(S2-1), (A1.1)+(B15)+(S2-1), (A1.1)+(B16)+(S2-1), (A1.1)+(B17)+(S2-1), (A1.1)+(B18)+(S2-1), (A1.1)+(B19)+(S2-1), (A1.1)+(B20)+(S2-1), (A1.1)+(B21)+(S2-1), (A1.1)+(B22)+(S2-1), (A1.1)+(B23)+(S2-1);

(A1.2)+(B1)+(S2-1), (A1.2)+(B2)+(S2-1), (A1.2)+(B3)+(S2-1), (A1.2)+(B4)+(S2-1), (A1.2)+(B5)+(S2-1), (A1.2)+(B6)+(S2-1), (A1.2)+(B7)+(S2-1), (A1.2)+(B8)+(S2-1), (A1.2)+(B9)+(S2-1), (A1.2)+(B10)+(S2-1), (A1.2)+(B11)+(S2-1), (A1.2)+(B12)+(S2-1), (A1.2)+(B13)+(S2-1), (A1.2)+(B14)+(S2-1), (A1.2)+(B15)+(S2-1), (A1.2)+(B16)+(S2-1), (A1.2)+(B17)+(S2-1), (A1.2)+(B18)+(S2-1), (A1.2)+(B19)+(S2-1), (A1.2)+(B20)+(S2-1), (A1.2)+(B21)+(S2-1), (A1.2)+(B22)+(S2-1), (A1.2)+(B23)+(S2-1);

(A2.1)+(B1)+(S2-1), (A2.1)+(B2)+(S2-1), (A2.1)+(B3)+(S2-1), (A2.1)+(B4)+(S2-1), (A2.1)+(B5)+(S2-1), (A2.1)+(B6)+(S2-1), (A2.1)+(B7)+(S2-1), (A2.1)+(B8)+(S2-1), (A2.1)+(B9)+(S2-1), (A2.1)+(B10)+(S2-1), (A2.1)+(B1)+(S2-1), (A2.1)+(B12)+(S2-1), (A2.1)+(B13)+(S2-1), (A2.1)+(B14)+(S2-1), (A2.1)+(B15)+(S2-1), (A2.1)+(B16)+(S2-1), (A2.1)+(B17)+(S2-1), (A2.1)+(B18)+(S2-1), (A2.1)+(B19)+(S2-1), (A2.1)+(B20)+(S2-1), (A2.1)+(B21)+(S2-1), (A2.1)+(B22)+(S2-1), (A2.1)+(B23)+(S2-1);

(A2.2)+(B1)+(S2-1), (A2.2)+(B2)+(S2-1), (A2.2)+(B3)+(S2-1), (A2.2)+(B4)+(S2-1), (A2.2)+(B5)+(S2-1), (A2.2)+(B6)+(S2-1), (A2.2)+(B7)+(S2-1), (A2.2)+(B8)+(S2-1), (A2.2)+(B9)+(S2-1), (A2.2)+(B10)+(S2-1), (A2.2)+(B11)+(S2-1), (A2.2)+(B12)+(S2-1), (A2.2)+(B13)+(S2-1), (A2.2)+(B14)+(S2-1), (A2.2)+(B15)+(S2-1), (A2.2)+(B16)+(S2-1), (A2.2)+(B17)+(S2-1), (A2.2)+(B18)+(S2-1), (A2.2)+(B19)+(S2-1), (A2.2)+(B20)+(S2-1), (A2.2)+(B21)+(S2-1), (A2.2)+(B22)+(S2-1), (A2.2)+(B23)+(S2-1);

(A1.1)+(A2.1)+(B1)+(S2-1), (A1.1)+(A2.1)+(B2)+(S2-1), (A1.1)+(A2.1)+(B3)+(S2-1), (A1.1)+(A2.1)+(B4)+(S2-1), (A1.1)+(A2.1)+(B5)+(S2-1), (A1.1)+(A2.1)+(B6)+(S2-1), (A1.1)+(A2.1)+(B7)+(S2-1), (A1.1)+(A2.1)+(B8)+(S2-1), (A1.1)+(A2.1)+(B9)+(S2-1), (A1.1)+(A2.1)+(B10)+(S2-1), (A1.1)+(A2.1)+(B11)+(S2-1), (A1.1)+(A2.1)+(B12)+(S2-1), (A1.1)+(A2.1)+(B13)+(S2-1), (A1.1)+(A2.1)+(B14)+(S2-1), (A1.1)+(A2.1)+(B15)+(S2-1), (A1.1)+(A2.1)+(B16)+(S2-1), (A1.1)+(A2.1)+(B17)+(S2-1), (A1.1)+(A2.1)+(B18)+(S2-1), (A1.1)+(A2.1)+(B19)+(S2-1), (A1.1)+(A2.1)+(B20)+(S2-1), (A1.1)+(A2.1)+(B21)+(S2-1), (A1.1)+(A2.1)+(B22)+(S2-1), (A1.1)+(A2.1)+(B23)+(S2-1);

(A1.1)+(A2.2)+(B1)+(S2-1), (A1.1)+(A2.2)+(B2)+(S2-1), (A1.1)+(A2.2)+(B3)+(S2-1), (A1.1)+(A2.2)+(B4)+(S2-1), (A1.1)+(A2.2)+(B5)+(S2-1), (A1.1)+(A2.2)+(B6)+(S2-1), (A1.1)+(A2.2)+(B7)+(S2-1), (A1.1)+(A2.2)+(B8)+(S2-1), (A1.1)+(A2.2)+(B9)+(S2-1), (A1.1)+(A2.2)+(B10)+(S2-1), (A1.1)+(A2.2)+(B11)+(S2-1), (A1.1)+(A2.2)+(B12)+(S2-1), (A1.1)+(A2.2)+(B13)+(S2-1), (A1.1)+(A2.2)+(B14)+(S2-1), (A1.1)+(A2.2)+(B15)+(S2-1), (A1.1)+(A2.2)+(B16)+(S2-1), (A1.1)+(A2.2)+(B17)+(S2-1), (A1.1)+(A2.2)+(B18)+(S2-1), (A1.1)+(A2.2)+(B19)+(S2-1), (A1.1)+(A2.2)+(B20)+(S2-1), (A1.1)+(A2.2)+(B21)+(S2-1), (A1.1)+(A2.2)+(B22)+(S2-1), (A1.1)+(A2.2)+(B23)+(S2-1);

(A2.1)+(A1.2)+(B1)+(S2-1), (A2.1)+(A1.2)+(B2)+(S2-1), (A2.1)+(A1.2)+(B3)+(S2-1), (A2.1)+(A1.2)+(B4)+(S2-1), (A2.1)+(A1.2)+(B5)+(S2-1), (A2.1)+(A1.2)+(B6)+(S2-1), (A2.1)+(A1.2)+(B7)+(S2-1), (A2.1)+(A1.2)+(B8)+(S2-1), (A2.1)+(A1.2)+(B9)+(S2-1), (A2.1)+(A1.2)+(B10)+(S2-1), (A2.1)+(A1.2)+(B11)+(S2-1), (A2.1)+(A1.2)+(B12)+(S2-1), (A2.1)+(A1.2)+(B13)+(S2-4), (A2.1)+(A1.2)+(B14)+(S2-1), (A2.1)+(A1.2)+(B15)+(S2-1), (A2.1)+(A1.2)+(B16)+(S2-1), (A2.1)+(A1.2)+(B17)+(S2-1), (A2.1)+(A1.2)+(B18)+(S2-1), (A2.1)+(A1.2)+(B19)+(S2-1), (A2.1)+(A1.2)+(B20)+(S2-1), (A2.1)+(A1.2)+(B21)+(S2-1), (A2.1)+(A1.2)+(B22)+(S2-1), (A2.1)+(A1.2)+(B23)+(S2-1);

(A2.1)+(A2.2)+(B1)+(S2-1), (A2.1)+(A2.2)+(B2)+(S2-1), (A2.1)+(A2.2)+(B3)+(S2-1), (A2.1)+(A2.2)+(B4)+(S2-1), (A2.1)+(A2.2)+(B5)+(S2-1), (A2.1)+(A2.2)+(B6)+(S2-1), (A2.1)+(A2.2)+(B7)+(S2-1), (A2.1)+(A2.2)+(B8)+(S2-1), (A2.1)+(A2.2)+(B9)+(S2-1), (A2.1)+(A2.2)+(B10)+(S2-1), (A2.1)+(A2.2)+(B11)+(S2-1), (A2.1)+(A2.2)+(B12)+(S2-1), (A2.1)+(A2.2)+(B13)+(S2-1), (A2.1)+(A2.2)+(B14)+(S2-1), (A2.1)+(A2.2)+(B15)+(S2-1), (A2.1)+(A2.2)+(B16)+(S2-1), (A2.1)+(A2.2)+(B17)+(S2-1), (A2.1)+(A2.2)+(B18)+(S2-1), (A2.1)+(A2.2)+(B19)+(S2-1), (A2.1)+(A2.2)+(B20)+(S2-1), (A2.1)+(A2.2)+(B21)+(S2-1), (A2.1)+(A2.2)+(B22)+(S2-1), (A2.1)+(A2.2)+(B23)+(S2-1).

It may be advantageous to combine one or more compounds (A) with a plurality of compounds (B) or a plurality of compounds (A) with one or more compounds (B). Furthermore, the combinations according to the invention can be used together with other agrochemically active compounds, for example from the group of the safeners, fungicides, herbicides, insecticides and plant growth regulators, or with formulation auxiliaries and additives customary in crop protection. Additives are, for example, fertilizers and colorants.

The combinations according to the invention (=herbicidal compositions) have an outstanding herbicidal activity against a broad spectrum of economically important monocotyledonous and dicotyledonous harmful plants. The active compounds also act efficiently on perennial weeds which produce shoots from rhizomes, rootstocks or other perennial organs and which are difficult to control. In this context, it does not matter whether the substances are applied before sowing, pre-emergence or post-emergence, for example together or separately. Post-emergence application, or early post-sowing pre-emergence application, is preferred.

Specifically, examples may be mentioned of some representatives of the monocotyledonous and dicotyledonous weed flora which can be controlled by the combinations according to the invention, without the enumeration being a restriction to certain species.

Examples of weed species on which the herbicidal compositions act efficiently are, from amongst the monocotyledonous weed species, for example *Avena* spp., *Alopecurus* spp., *Brachiaria* spp., *Digitaria* spp., *Lolium* spp., *Equinochloa* spp., *Panicum* spp., *Phalaris* spp., *Poa* spp., *Setaria* spp. and also *Bromus* spp., such as *Bromus catharticus, Bromus secalinus, Bromus erectus, Bromus tectorum* and *Bromus japonicus*, and *Cyperus* species from the annual group, and, amongst the perennial species, *Agropyron, Cynodon, Imperata* and *Sorghum* and also perennial *Cyperus* species.

In the case of the dicotyledonous weed species, the spectrum of action extends to species such as, for example, *Abutilon* spp., *Amaranthus* spp., *Chenopodium* spp., *Chrysanthemum* spp., *Galium* spp. such as *Galium aparine, Ipomoea* spp., *Kochia* spp., *Lamium* spp., *Matricaria* spp., *Pharbitis* spp., *Polygonum* spp., *Sida* spp., *Sinapis* spp., *Solanum* spp., *Stellaria* spp., *Veronica* spp. and *Viola* spp., *Xanthium* spp., amongst the annuals, and *Convolvulus, Cirsium, Rumex* and *Artemisia* in the case of the perennial weeds.

If the herbicide combinations according to the invention are applied to the soil surface before germination, then the weed seedlings are either prevented completely from emerging, or the weeds grow until they have reached the cotyledon stage but then their growth stops, and, eventually, after three to four weeks have elapsed, they die completely.

If the active compounds are applied post-emergence to the green parts of the plants, growth likewise stops drastically a very short time after the treatment and the weed plants remain at the growth stage of the point of time of application, or they die completely after a certain time, so that in this manner competition by the weeds, which is harmful to the crop plants, is eliminated at a very early point in time and in a sustained manner.

The herbicidal compositions according to the invention are distinguished by a rapidly commencing and long-lasting herbicidal action. As a rule, the rainfastness of the active compounds in the combinations according to the invention is advantageous. A particular advantage is that the dosages of the compounds (A) and (B), which are used in the combinations and are effective, can be adjusted to such a low quantity that their soil action is optimally low. Not only does this allow them to be employed in sensitive crops in the first place, but groundwater contaminations are virtually avoided. The active-ingredient combination according to the invention allows the application rate of the active compounds required to be reduced considerably.

In a preferred embodiment, when herbicides of the type (A)+(B) are used jointly, superadditive (=synergistic) effects are observed. This means that the effect in the combinations exceeds the expected total of the effects of the individual herbicides employed. The synergistic effects allow the application rate to be reduced, a broader spectrum of broad-leaved weeds and grass weeds to be controlled, the herbicidal action to take place more-rapidly, the duration of action to be longer, the harmful plants to be controlled better while using only one, or few, applications, and the application period which is possible to be extended.

The abovementioned properties and advantages are of benefit for weed control practice to keep agricultural crops free from undesired competing plants and thus to safeguard and/or increase the yields from the qualitative and quantitative point of view. These novel combinations markedly exceed the technical state of the art with a view to the properties described.

While the combinations according to the invention have an outstanding herbicidal activity against monocotyledonous and dicotyledonous weeds, the crop plants are damaged only to a minor extent, if at all.

Moreover, some of the compositions according to the invention have outstanding growth-regulatory properties on the crop plants. They engage in the plants' metabolism in a regulatory manner and can thus be employed for provoking directed effects on plant constituents and to facilitate harvesting such as for example by triggering desiccation and stunted growth. Moreover, they are also suitable for the general control and inhibition of undesired vegetative growth without simultaneously destroying the plants. An inhibition of vegetative growth is very important in a large number of monocotyledonous and dicotyledonous crops since yield losses as a result of lodging can thus be reduced, or prevented completely.

Owing to their herbicidal and plant-growth-regulatory properties, the compositions according to the invention can be employed for controlling harmful plants in genetically modified crop plants or crop plants obtained by mutation/selection. These crop plants are distinguished as a rule by particular, advantageous properties, such as resistances to herbicidal compositions or resistances to plant diseases or causative agents of plant diseases such as particular insects or microorganisms such as fungi, bacteria or viruses. Other particular properties relate, for example, to the harvested material with regard to quantity, quality, storability, composition and specific constituents. Thus, for example, transgenic plants are known whose starch content is increased or whose starch quality is altered, or those where the harvested material has a different fatty acid composition.

Conventional methods of generating novel plants which have modified properties in comparison to plants occurring to date consist, for example, in traditional breeding methods and the generation of mutants (see, for example, U.S. Pat. No. 5,162,602; U.S. Pat. No. 4,761,373; U.S. Pat. No. 4,443,971). Alternatively, novel plants with altered properties can be generated with the aid of recombinant methods (see, for example, EP-A-0221044, EP-A-0131624). For example, the following have been described in several cases:

the modification, by recombinant technology, of crop plants with the aim of modifying the starch synthesized in the plants (for example WO 92/11376, WO 92/14827, WO 91/19806), transgenic crop plants which exhibit resistances to other herbicides, for example to sulfonylureas (EP-A-0257993, U.S. Pat. No. 5,013,659), transgenic crop plants with the capability of producing *Bacillus thuringiensis* toxins (Bt toxins), which make the plants resistant to certain pests (EP-A-0142924, EP-A-0193259), transgenic crop plants with a modified fatty acid composition (WO 91/13972).

A large number of techniques in molecular biology are known in principle with the aid of which novel transgenic plants with modified properties can be generated: see, for example, Sambrook et al., 1989, Molecular Cloning, A Laboratory Manual, $2^{nd}$ Edition, Cold Spring Harbor Laboratory Press, Cold Spring Harbor, N.Y.; or Winnacker "Gene und Klone", V C H Weinheim $2^{nd}$ Edition 1996 or Christou, "Trends in Plant Science" 1 (1996) 423-431).

To carry out such recombinant manipulations, nucleic acid molecules which allow mutagenesis or sequence changes by recombination of DNA sequences can be introduced into plasmids. For example, the abovementioned standard methods allow base exchanges to be carried out, subsequences to be removed, or natural or synthetic sequences to be added. To connect the DNA fragments to each other, adapters or linkers may be added to the fragments.

For example, the generation of plant cells with a reduced activity of a gene product can be achieved by expressing at least one corresponding antisense RNA, a sense RNA for achieving a cosuppression effect or by expressing at least one suitably constructed ribosome which specifically cleaves transcripts of the abovementioned gene product.

To this end, it is possible to use DNA molecules which encompass the entire coding sequence of a gene product inclusive of any flanking sequences which may be present, and also DNA molecules which only encompass portions of the coding sequence, it being necessary for these portions to be long enough to have an antisense effect in the cells. The use of DNA sequences which have a high degree of homology to the encoding sequences of a gene product, but are not completely identical to them, is also possible.

When expressing nucleic acid molecules in plants, the protein synthesized can be localized in any desired compartment of the plant cell. However, to achieve localization in a particular compartment, it is possible, for example, to link the coding region with DNA sequences which ensure localization in a particular compartment. Such sequences are known to those skilled in the art (see, for example, Braun et al., EMBO J. 11 (1992), 3219-3227; Wolter et al., Proc. Natl. Acad. Sci. USA 85 (1988), 846-850; Sonnewald et al., Plant J. 1 (1991), 95-106).

The transgenic plant cells can be regenerated by known techniques to give rise to intact plants. In principle, the transgenic plants can be plants of any desired plant species, i.e. not only monocotyledonous, but also dicotyledonous, plants. Thus, transgenic plants can be obtained whose properties are altered by overexpression, suppression or inhibition of homologous (=natural) genes or gene sequences or the expression of heterologous (=foreign) genes or gene sequences.

The invention therefore also relates to a method of controlling undesired vegetation, preferably in plant crops such as cereals (e.g. wheat, barley, rye, oats, rice, corn, millet), sugar beet, sugar cane, oilseed rape, cotton and soya beans, especially preferably in monocotyledonous crops such as cereals, for example wheat, barley, rye, oats, rice, corn and millet, which comprises applying one or more herbicides of type (A) together with one or more herbicides of type (B) to the harmful plants, parts of these plants, plant seeds or the area where the plants grow, for example the area under cultivation.

The plant crops can also have been genetically modified or been obtained by mutation selection and are preferably tolerant to acetolactate synthase (ALS) inhibitors.

The invention also relates to the use of the inventive combinations of compounds (A)+(B) for controlling harmful plants, preferably in plant crops.

The herbicidal compositions according to the invention can also be used non-selectively for controlling unwanted vegetation, for example in plantation crops, in the borders of paths, in squares, in industrial plants or in railroad instalations.

The active compound combinations according to the invention can exist not only as mixed formulations of the two components (A) and (B), if appropriate together with further agrochemically active compounds, additives and/or customary formulation auxiliaries, which are then applied in the customary manner as a dilution with water, but also as so-called tank mixes by jointly diluting the separately formulated, or partially separately formulated, components with water.

The compounds (A) and (B) or their combinations can be formulated in various ways, depending on the prevailing biological and/or chemical-physical parameters. The following are examples of general possibilities for formulations: wettable powders (WP), water-soluble concentrates, emulsifiable concentrates (EC), aqueous solutions (SL), emulsions (EW) such as oil-in-water and water-in-oil emulsions, sprayable solutions or emulsions, suspension concentrates (SC), oil- or water-based dispersions, suspoemulsions, dusts (DP), seed-dressing materials, granules for soil application or for broadcasting, or water-dispersible granules (WG), ULV formulations, microcapsules or waxes.

The individual formulation types are known in principle and are described for example, in: Winnacker-Küchler, "Chemische Technologie", Volume 7, C. Hauser Verlag Munich, 4th Edition, 1986; van Valkenburg, "Pesticide Formulations", Marcel Dekker N.Y., 1973; K. Martens, "Spray Drying Handbook", 3rd Ed. 1979, G. Goodwin Ltd. London.

The formulation auxiliaries required, such as inert materials, surfactants, solvents and other additives are also known and are described, for example, in Watkins, "Handbook of Insecticide Dust Diluents and Carriers", 2nd Ed., Darland Books, Caldwell, N.J.; H. v. Olphen, "Introduction to Clay Colloid Chemistry"; 2nd Ed., J. Wiley & Sons, N.Y. Marsden, "Solvents Guide", 2nd Ed., Interscience, N.Y. 1950; McCutcheon's, "Detergents and Emulsifiers Annual", MC Publ. Corp., Ridgewood, N.J.; Sisley and Wood, "Encyclopedia of Surface Active Agents", Chem. Publ. Co. Inc., N.Y. 1964; Schönfeldt, "Grenzflächenaktive Äthylenoxidadukte" [Surface-active ethylene oxide adducts], Wiss. Verlagsgesellschaft, Stuttgart 1976, Winnacker-Küchler, "Chemische Technologie", Volume 7, C. Hauser Verlag Munich, 4th Edition 1986.

Based on these formulations, combinations with other agrochemically active substances, such as other herbicides, fungicides or insecticides, and with safeners, fertilizers and/or growth regulators, may also be prepared, for example in the form of a readymix or a tank mix.

Wettable powders (sprayable powders) are products which are uniformly dispersible in water and which, besides the active compound, also comprise ionic or nonionic surfactants (wetters, dispersants), for example polyoxethylated alkylphenols, polyethoxylated fatty alcohols or fatty amines, alkanesulfonates or alkylbenzenesulfonates, sodium lignosulfonate, sodium 2,2'-dinaphthylmethane-6,6'-disulfonate, sodium dibutylnaphthalenesulfonate or else sodium oleoylmethyltauride, in addition to a diluent or inert material.

Emulsifiable concentrates are prepared by dissolving the active compound in an organic solvent, for example butanol, cyclohexanone, dimethylformamide, xylene or else higher-boiling aromatics or hydrocarbons with addition of one or more ionic or nonionic surfactants (emulsifiers). Examples of emulsifiers which may be used are: calcium salts of alkylarylsulfonic acids, such as calcium dodecylbenzene sulfonate, or nonionic emulsifiers such as fatty acid polyglycol esters, alkylaryl polyglycol ethers, fatty alcohol polyglycol ethers, propylene oxide/ethylene oxide condensates, alkyl polyethers, sorbitan fatty acid esters, polyoxyethylene sorbitan fatty acid esters or polyoxethylene sorbitol esters.

Dusts are obtained by grinding the active compound with finely divided solid materials, for example talc, natural clays such as kaolin, bentonite and pyrophyllite, or diatomaceous earth.

Suspension concentrates (SC) can be water- or oil-based. They can be prepared, for example, by wet grinding by means of commercially available bead mills and, if appropriate, addition of further surfactants as they have already been mentioned for example above in the case of the other formulation types.

Emulsions, for example oil-in-water emulsions (EW), can be prepared for example by means of stirrers, colloid mills and/or static mixers using aqueous organic solvents and, if appropriate, further surfactants as have already been mentioned for example above in the case of the other formulation types.

Granules can be prepared either by spraying the active compound onto adsorptive, granulated inert material or by applying active compound concentrates to the surface of carriers such as sand, kaolinites or granulated inert-material with the aid of binders, for example polyvinyl alcohol, sodium polyacrylate or else mineral oils. Suitable active compounds may also be granulated in the manner conventionally used for the production of fertilizer granules, if desired in a mixture with fertilizers. As a rule, water-dispersible granules are prepared by customary processes such as spray drying, fluidized-bed granulation, disk granulation, mixing with high-speed mixers and extrusion without solid inert material. Regarding the production of disk granules, fluidized-bed granules, extruder granules and spray granules, see, for example, the methods in "Spray-Drying Handbook" 3rd ed. 1979, G. Goodwin Ltd., London; J. E. Browning, "Agglomeration", Chemical and Engineering 1967, page 147 et seq; "Perry's Chemical Engineer's Handbook", 5th Ed., McGraw-Hill, New York 1973, pp. 8-57.

As regards further details on the formulation of crop protection products, see, for example, G. C. Klingmam, "Weed Control as a Science", John Wiley and Sons, Inc., New York, 1961, pages 81-96 and J. D. Freyer, S. A. Evans, "Weed Control Handbook", 5th Ed., Blackwell Scientific Publications, Oxford, 1968, pages 101-103.

As a rule, the agrochemical formulations comprise 0.1 to 99 percent by weight, in particular 2 to 95% by weight, of active compounds of the types A and/or B, the following concentrations being customary, depending on the type of formulation:

The active compound concentration in wettable powders is, for example, approximately 10 to 95% by weight, the remainder to 100% by weight being composed of customary formulation constituents. In the case of emulsifiable concentrates, the active compound concentration may amount to, for example, 5 to 80% by weight. Formulations in the form of dusts comprise, in most cases, 5 to 20% by weight of active compound, sprayable solutions approximately 0.2 to 25% by weight of active compound. In the case of granules such as dispersible granules, the active compound content depends partly on whether the active compound is present in liquid or solid form and on which granulation auxiliaries and fillers are being used. As a rule, the content amounts to between 10 and 90% by weight in the case of the water-dispersible granules.

In addition, the abovementioned active compound formulations may comprise, if appropriate, the conventional adhesives, wetters, dispersants, emulsifiers, preservatives, antifreeze agents, solvents, fillers, colorants, carriers, antifoams, evaporation inhibitors, pH regulators or viscosity regulators.

The herbicidal action of the herbicide combinations according to the invention can be improved, for example, by surfactants, preferably by wetters from the group of the fatty alcohol polyglycol ethers. The fatty alcohol polyglycol ethers preferable contain 10-18 carbon atoms in the fatty alcohol radical and 2-20 ethylene oxide units in the polyglycol ether moiety. The fatty alcohol polyglycol ethers can be nonionic or ionic, for example in the form of fatty alcohol polyglycol ethers sulfates, which can be used, for example, as alkali metal salts (e.g. sodium salts or potassium salts) or ammonium salts, but also as alkaline earth metal salts such as magnesium salts, such as sodium $C_{12}/C_{14}$-fatty alcohol diglycol ether sulfate (Genapol® LRO, Clariant); see, for example, EP-A-0476555, EP-A-0048436, EP-A-0336151 or U.S. Pat. No. 4,400,196 and also Proc. EWRS Symp. "Factors Affecting Herbicidal Activity and Selectivity", 227-232 (1988). Nonionic fatty alcohol polyglycol ethers are, for example, $(C_{10}$-$C_{18})$—, preferably $(C_{10}$-$C_{14})$-fatty alcohol polyglycol ethers containing 2-20, preferably 3-15, ethylene oxide units (e.g. isotridecyl alcohol polyglycol ether), for example from the Genapol® series, such as Genapol® X-030, Genapol® X-060, Genapol® X-080 or Genapol® X-150 (all from Clariant GmbH). Moreover, it is known that fatty alcohol polyglycol ethers such as nonionic or ionic fatty alcohol polyglycol ethers (for example fatty alcohol polyglycol ether sulfates) are also suitable as penetrants and synergists for a number of other herbicides, inter alia also herbicides from the group of the imidazolinones; (see, for example, EP-A-0502014).

The herbicidal effect can also be increased using vegetable oils. The term vegetable oils is to be understood as meaning oils from oil-plant species, such as soya oil, rapeseed oil, corn oil, sunflower oil, cottonseed oil, linseed oil, coconut oil, palm oil, safflower oil or castor oil, in particular rapeseed oil, and their transesterification products, for example alkyl esters, such as rapeseed oil methyl ester or rapeseed oil ethyl ester.

The vegetable oils are preferably esters of $C_{10}$-$C_{22}$-, preferably $C_{12}$-$C_{20}$-fatty acids. The $C_{10}$-$C_{22}$-fatty acid esters are, for example, esters of unsaturated or saturated $C_{10}$-$C_{22}$-fatty acids, in particular those with an even number of carbon atoms, for example erucic acid, lauric acid, palmitic acid and, in particular, $C_{18}$-fatty acids such as stearic acid, oleic acid, linoleic acid or linolenic acid.

Examples of $C_{10}$-$C_{22}$-fatty acid esters are esters obtained by reacting glycerol or glycol with the $C_{10}$-$C_{22}$-fatty acids as they exist, for example in oils from oil-plant species, or $C_1$-$C_{20}$-alkyl-$C_{10}C_{22}$-fatty acid esters as can be obtained, for example, by transesterification of the abovementioned glycerol- or glycol-$C_{10}$-$C_{22}$-fatty acid esters with $C_1$-$C_{20}$-alcohols (for example methanol, ethanol, propanol or butanol). Transesterification can be carried out by known methods as are described, for example, in Römpp Chemie Lexikon, 9th edition, volume 2, page 1343, Thieme Verlag Stuttgart.

Preferred $C_1$-$C_{20}$-alkyl-$C_{10}$-$C_{22}$-fatty acid esters are the methyl, ethyl, propyl, butyl, 2-ethylhexyl and dodecyl esters. Preferred glycol- and glycerol-$C_{10}$-$C_{22}$-fatty acid esters are the uniform or mixed glycol esters and glycerol esters of $C_{10}$-$C_{22}$-fatty acids, in particular those fatty acids which have an even number of carbon atoms, for example erucic acid, lauric acid, palmitic acid and, in particular, $C_{18}$-fatty acids such as stearic acid, oleic acid, linolic acid or linolenic acid.

The vegetable oils can be present in the herbicidal compositions according to the invention for example in the form of commercially available oil-containing formulation additives, in particular those based on rapeseed oil such as Hasten® (Victorian Chemical Company, Australia, hereinbelow termed Hasten, main constituent: rapeseed oil ethyl ester), Actirob®B (Novance, France, hereinbelow termed ActirobB, main constituent: rapeseed oil methyl ester), Rako-Binol® (Bayer AG, Germany, termed Rako-Binol hereinbelow, main constituent: rapeseed oil), Renol® (Stefes, Germany, termed Renol hereinbelow, vegetable oil constituent: rapeseed oil methyl ester), or Stefes Mero® (Stefes, Germany, hereinbelow termed Mero, main constituent: rapeseed oil methyl ester).

For use, the formulations, which are present in commercially available form, are optionally diluted in the customary manner, for example using water in the case of wettable powders, emulsifiable concentrates, dispersions and water-dispersible granules. Preparations in the form of dusts, soil granules, granules for broadcasting and sprayable solutions are usually not diluted further with other inert substances prior to use.

The active compounds can be applied to the plants, parts of the plants, seeds of the plants or the area under cultivation (soil of a field), preferably to the green plants and parts of the plants and, if appropriate, additionally to the soil of the field. One possible use is the joint application of the active compounds in the form of tank mixes, the concentrated formulations of the individual active compounds, in optical formulations, jointly being mixed with water in the tank and the resulting spray mixture being applied.

A joint herbicidal formulation of the combination according to the invention of the active compounds (A) and (B) has the advantage of being easier to apply since the quantities of the components are already presented in the correct ratio to each other. Moreover, the adjuvants in the formulation can be matched optimally to each other, while a tank mix of different formulations may lead to undesired combinations of adjuvants.

A. General Formulation Examples a) A dust is obtained by mixing 10 parts by weight of an active compound/active compound mixture and 90 parts by weight of talc as inert material and comminuting the mixture in a hammer mill.

b) A wettable powder which is readily dispersible in water is obtained by mixing 25 parts by weight of an active compound/active compound mixture, 64 parts by weight of kaolin-containing quartz as inert material, 10 parts by weight of potassium lignosulfonate and 1 part by weight of sodium oleoylmethyltaurinate as wetter and dispersant, and grinding the mixture in a pinned-disk mill.

c) A dispersion concentrate which is readily dispersible in water is obtained by mixing 20 parts by weight of an active compound/active compound mixture with 6 parts by weight of alkylphenol polyglycol ether (® Triton X 207), 3 parts by weight of isotridecanol polyglycol ether (8 EO) and 71 parts by weight of paraffinic mineral oil (boiling range for example approx. 255 to 277° C.), and grinding the mixture in a ball mill to a fineness of below 5 microns.

d) An emulsifiable concentrate is obtained from 15 parts by weight of an active compound/active compound mixture, 75 parts by weight of cyclohexanone as solvent and 10 parts by weight of oxethylated nonylphenol as emulsifier.

e) Water-dispersible granules are obtained by mixing
   75 parts by weight of an active compound/active compound mixture,
   10 parts by weight of calcium lignosulfonate,
   5 parts by weight of sodium lauryl sulfate,
   3 parts by weight of polyvinyl alcohol and
   7 parts by weight of kaolin,
   grinding the mixture on a pinned-disk mill and granulating the powder in a fluidized bed by spraying on water as granulation liquid.

f) Water-dispersible granules are also obtained by homogenizing and precomminuting, in a colloid mill,
   25 parts by weight of an active compound/active compound mixture,
   5 parts by weight of sodium 2,2'-dinaphthylmethane-6,6'-disulfonate,
   2 parts by weight of sodium oleoylmethyltaurinate,
   1 part by weight of polyvinyl alcohol,
   17 parts by weight of calcium carbonate and
   50 parts by weight of water,
   subsequently grinding the mixture in a bead mill and atomizing and drying the resulting suspension in a spray tower by means of a single-substance nozzle.

B. Biological Examples

Herbicidal Action (Outdoor Trials)

The seeds or rhizome pieces of typical harmful plants were planted and grown under natural outdoor conditions. After the harmful plants had emerged, they were treated, as a rule at the 2- to 4-leaf stage, with various dosages of the compositions according to the invention at a water application rate of 100 to 400 l/ha (converted).

After the treatment (approx. 4-6 weeks after application), the herbidical activity of the active compounds or active compound mixtures was scored visually by comparing the treated plots with the untreated control plots. Damage and development of all above-ground parts of the plants was recorded. Scoring was done on a percentage scale (100% action=all plants dead; 50% action=50% of the plants and green plant parts dead; 0% action=no discernible action=like control plot). The score figures of in each case 4 plots were averaged.

The results are listed in the tables below, where the activity measured for the independent use of the active compounds (A) and (B) is stated in brackets and where g of AS/ha denotes grams of active substance per hectare.

EXAMPLE 1

| Active compound(s) | g of AS/ha | Setaria viridis % activity | Wheat % damage |
|---|---|---|---|
| A) (A1.1)$^S$ | 7.5 | 35 | 0 |
| B) flucarbazone (B1) | 10 | 40 | 5 |
| A + B | 7.5 + 10 | 85 (35 + 40) | 5 |

(A1.1)$^S$ = mesosulfuron-methyl (A1.1) + safener mefenpyr-diethyl (S1-1)

EXAMPLE 2

| Active compound(s) | g of AS/ha | Veronica hederifolia % activity | Wheat % damage |
|---|---|---|---|
| A) (A1.1)$^S$ | 5 | 30 | 0 |
| B) picolinafen (B6) | 30 | 65 | 0 |
| A + B | 5 + 30 | 98 (30 + 65) | 1 |
| C) cinidon-ethyl (B7) | 50 | 25 | 5 |
| A + C | 5 + 50 | 75 (30 + 25) | 5 |

(A1.1)$^S$ = mesosulfuron-methyl (A1.1) + safener mefenpyr-diethyl (S1-1)

EXAMPLE 3

| Active compound(s) | g of AS/ha | Veronica hederifolia % damage | Wheat % activity |
|---|---|---|---|
| A) (A2.2)$^S$ | 2.5 | 0 | 0 |
| B) cinidon-ethyl (B7) | 25 | 35 | 0 |
| A + B | 2.5 + 25 | 65 (0 + 35) | 0 |
| C) picolinafen (B6) | 5 | 55 | 0 |
| A + C | 2.5 + 5 | 75 (0 + 55) | 0 |
| D) florasulam (B3) | 4 | 60 | 0 |
| A + D | 2.5 + 4 | 65 (0 + 60) | 0 |

(A2.2)$^S$ = iodinosulfuron-methyl sodium (A2.2) + safener mefenpyr-diethyl (S1-1)

We claim:

1. A synergistic herbicide combination comprising an effective amount of components (A) and (B), where
(A) denotes a compound of the formula (I) and their salts

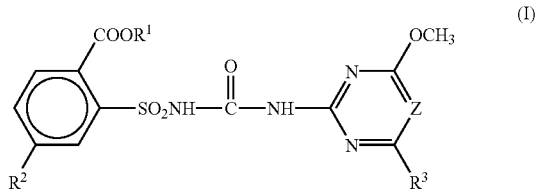

in which
R¹ is methyl,
R² is CH₂NHSO₂CH₃,
R³ is methoxy and
Z is CH;
and
(B) denotes one or more herbicides which act selectively in some monocotyledonous crops against monocotyledonous and/or dicotyledonous harmful plants, which herbicides are selected from the group of compounds consisting of procarbazone, florasulam and flufenacet.

2. The herbicide combination as claimed in claim 1 which comprises, as component (A), one or more compounds selected from the group consisting of mesosulfuron-methyl and mesosulfuron-methyl sodium.

3. The herbicide combination as claimed in claim 1 which additionally comprises one or more further components selected from the group consisting of agrochemically active compounds of a different type, formulation auxiliaries and additives customary in crop protection.

4. The herbicide combination as claimed in claim 1 which additionally comprises one or more safeners.

5. A method for controlling harmful plants which comprises applying a herbicide combination as defined in claim 1 onto the plants, parts of plants, plant seeds or the area where the plant grows.

6. The method as claimed in claim 5 for the selective control of harmful plants in plant crops.

7. The method as claimed in claim 6 for the control of harmful plants in crops of monocotyledonous plants.

8. The method as claimed in claim 6 in which the plant crops are genetically modified or have been obtained by mutation/selection.

9. The herbicide combination as claimed in claim 2, wherein component (B) is selected from the group consisting of procarbazone, flufenacet, and florasulam.

10. The herbicide combination as claimed in claim 9, wherein component (B) is procarbazone.

11. The herbicide combination as claimed in claim 9, wherein component (B) is flufenacet.

12. The herbicide combination as claimed in claim 9, wherein component (B) is florasulam.

13. The herbicide combination as claimed in claim 1, wherein component (A) is mesosulfuron-methyl and component (B) is procarbazone.

14. The herbicide combination as claimed in claim 1, wherein the component (A) is mesosulfuron-methyl and component (B) is flufenacet.

15. The herbicide combination as claimed in claim 1, wherein the component (A) is mesosulfuron-methyl and component (B) is florasulam.

* * * * *